United States Patent [19]

Porro et al.

[11] Patent Number: 4,711,779
[45] Date of Patent: Dec. 8, 1987

[54] GLYCOPROTEINIC CONJUGATES HAVING TRIVALENT IMMUNOGENIC ACTIVITY

[75] Inventors: Massimo Porro, Localita' Collanza; Paolo Costantino, Colle Val d'Elsa, both of Italy

[73] Assignee: Sclavo S.p.A., Siena, Italy

[21] Appl. No.: 881,091

[22] Filed: Jul. 2, 1986

[30] Foreign Application Priority Data

Jul. 5, 1985 [IT] Italy ................. 21451 A/85

[51] Int. Cl.⁴ ............. C07K 17/10; A61K 39/385
[52] U.S. Cl. ............................. 424/92; 530/395; 530/397; 530/406
[58] Field of Search ............ 424/92; 530/395, 406, 530/397

[56] References Cited

U.S. PATENT DOCUMENTS

| | | | |
|---|---|---|---|
| 4,057,685 | 11/1977 | McIntire | 424/92 X |
| 4,356,170 | 10/1982 | Jennings et al. | 424/92 |
| 4,496,538 | 1/1985 | Gordon | 424/92 |
| 4,619,828 | 10/1986 | Gordon | 424/92 |
| 4,663,160 | 5/1987 | Tsay et al. | 424/92 X |

OTHER PUBLICATIONS

"An Immunological Study of the Diphtheria Toxin Molecule", A. M. Pappenheimer, Jr., et al., Immunchem., vol. 9, pp. 891-906 (1972).
"Diptheria Toxin and Related Proteins", T. Uchida, et al., J. Bio. Chem., vol. 248, No. 11, pp. 3838-3844 (1973).
"Pertussis Toxin", R. D. Sekura, et al., J. Bio. Chem., vol. 258, No. 23, pp. 14647-14651 (1983).
"Large-Scale Production of Tetanus Toxoid", P. A. Nielsen, J. App. Micro., pp. 453-454 (Mar. 1967).

*Primary Examiner*—Howard E. Schain
*Attorney, Agent, or Firm*—Hedman, Gibson, Costigan & Hoare

[57] ABSTRACT

Glycoproteinic conjugates having trivalent immunogenic activity obtained by binding, by a covalent bond, to a protein selected among CRM 197, tetanus toxoid, and pertussis toxin, at least an oligosaccharidic hapten derived from the capsular polysaccharide of a gram-positive bacterium and at least an oligosaccharidic hapten derived from the capsular polysaccharide of a gram-negative bacterium, and wherein said oligosaccharidic haptens are previously activated by introducing terminal esters.

12 Claims, 4 Drawing Figures

GLYCOPROTEINIC CONJUGATES HAVING TRIVALENT IMMUNOGENIC ACTIVITY

The present invention relates to glycoproteinic conjugates having trivalent immunogenic activity, to their preparation, and to their use as vaccines.

In particular, the present invention relates to glycoproteinic conjugates having trivalent immunogenic activity obtained by binding, by a covalent bond, to a protein selected among CRM 197, tetanus toxoid and pertussis toxin, at least one oligosaccharidic hapten derived from the capsular polysaccharide of a gram-positive bacterium, and at least one oligosaccharidic hapten derived from the capsular polysaccharide of a gram-negative bacterium, after the preliminary activation of said oligosaccharidic haptens by the introduction of terminal ester groups.

The development of vaccines against such capsulate bacteria as meningococcus and pneumococcus by the use of capsular polysaccharidic antigens derived from said bacteria, has shown the poor immunogenicity of said polysaccharidic anitgens, above all in infantile population.

This represents a problem of particular gravity and interest because the greatest level of incidence of infections caused by said capsulate bacteria occurs in children. From this the necessity derives of improving the immunogenic properties of capsular polysaccharides for the preparation of more effective vaccines.

The synthesis and the use of glycoproteinic conjugates represent a particularly interesting solution in improving the immune response to the polysaccharidic antigens.

Avery (J. Exp. Med. (1929) 50, 533) and Gobel (J. Exp. Med. (1939) 69, 53) described, about 50 years ago, the preparation and the use of glycoproteinic conjugates, demonstrating that the immunization of animals by the said compounds, wherein the saccharidic moiety way polysaccharide of *S. pneumoniae* Type 3, determined an immunization against the bacterium, which was more efficacious than that of polysaccharide as such.

Many studies have been recently published in the field of the synthesis of the glycoproteinic conjugates, and promising relusts have been obtained with *Haemophilus influenzae* Type b, and Meningococcus Group A and C.

U.S. Pat. No. 4,356,170 discloses and claims a glycoproteinic conjugate constituted by the capsular polysaccharide of an either gram-positive or gram-negative bacterium and by a protein, and a process for the prepartion thereof, characterized in that the capsular polysaccharide is modified, before being bound to the protein, so to generate terminal aldehydic groups by oxydation of vicinal hydroxy groups.

According to said techinque of the prior art, the glycoproteinic conjugates so objained can be used as vaccines against gram-positive or gram-negative bacteria, or for the preparation of multiple vaccines, i.e., vaccines with immune responses to different bacteria, by mixing two or more glycoconjugates in a pharmaceutically acceptable liquid carier.

It has been found now that, under particular conditions, binding is possible, to a same protein, oligosaccharidic haptens derived from capsular polysaccharides of gram-negative and gram-positive bacteria, a glycoproteinic conjugate having trivalent immunogenic activity being obtained.

Accordingly, the present invention relates to glycoproteinic conjugates having trivalent immunogenic activity, obtained by binding, by a covalent bond, to a protein selected among CRM 197, tetanus toxoid, pertussis toxin, at least one oligosaccharidic hapten derived from the capsular polysaccharide of a gram-positive bacterium, and at least one oligosaccharidic hapten derived from the capsular polysaccharide of a gram-negative bacterium, after the preliminary activation of the oligosaccharidic haptens by the introduction into them of terminal ester groups.

The glycoproteinic conjugates so obtained are capable of inducing on an animal model, contemporaneously, anamnestic immune responses to the capsular polysaccharidic antigen of gram-negative bacteria, to the capsular polysaccharidic antigen of gram-positive bacteria, as well as to the protein used. The conjugates of the present invention are useful to prepare novel vaccines against epidemiologically meaningful capsulate gram-negative and gram-positive bacteria, by using one single glycoproteinic conjugate having trivalent immunogenic activity.

According to the present invention, the proteins used for the preparation of the glycoproteinic conjugates having trivalent immunogenic activity, are selected among the proteins physiologically tolerated and with free amino groups.

Preferably, proteins having thymus-depending immunogenic activity are used.

Among these, particularly preferred are CRM 197, tetanus toxoid and pertussis toxin.

Said proteins are prepared by culturing the respective producer microorganisms, separating from the culture medium by filtration, precipitating and finally purifying them by chromatographic techniques.

According to the present invention, the oligosaccharidic haptens are selected among those derived from capsular polysaccharides of epidemiologically meaningful gram-positive and gram-negative bacteria.

Particularly suitable to the purpose are those derived from gram-positive bacteria belonging to the group of *Streptococcus pneumoniae, Streptococcus β-emoliticus,* and those derived from capsular polysaccharides of gram-negative bacteria belonging to the group of *Neisseria meningitidis, Pseudomonas aeruginosa, Escherichia coli* and *Haemophilus influenzae.*

The oligosaccharidic haptens are prepared by acidic hydrolysis of the corresponding capsular polysaccharidic antigens. Typically, the hydrolysis reaction is carried out by suspending the capsular polysaccharide in an aqueous solution of acetic acid at a pH value comprised within the range of from 3 to 5.5.

The hydrolysis is carried out by maintaining the solution inside sealed ampuls, at a temperature of 100° C., for a time of from 6 to 40 hours.

At the end of the hydrolysis reaction, the oligosaccharidic haptens are separated from the reaction mixture by gel-chromatography, and the effluents are analysed to determine the presence of methyl-pentoses, phosphorus and reducing groups.

The molecular weight of said oligosaccharidic haptens is determined by gel-chromatographic analysis, by measuring the distribution constant (Kd), whilst the characterization of the physical dimensions is carried out by N.M.R. analysis.

The immunochemical properties of said oligosaccharidic haptens are determined according to the method as disclosed by Porro et al. (Molec. Immunol., in press, 1985), which combines the technique of electrophoretic affinity with the "rocket" immunoelectrophoresis technique, and is based on the inhibiting capacity of the haptens in the immunoprecipitation reactions between the antigen and homologous antibodies.

Oligosaccharidic haptens suitable to the purpose are selected among those having a molecular weight of from $10^3$ to $2 \cdot 10^3$, preferably having a molecular weight of 1500, and characterized by the presence of terminal reducing groups.

According to the present invention, said oligosaccharidic haptens are activated by the introduction of terminal ester groups before being bound by covalent bonds to the protein.

The activation comprises the introduction of primary amino groups into the terminal reducing groups of the oligosaccharidic haptens, and the subsequent conversion of said amino groups into the corresponding esters.

The process is generally carried out by suspending the oligosaccharidic haptens in water in the presence of ammonium chloride and $NaBH_3CN$.

The solution so obtained is adjusted to a pH vlaue of from 7.5 to 9.5 and is kept, within sealed ampuls, at a temperature of from 30° C. to 55° C. for a corresponding time of from 1 to 2 weeks.

At the end of the reaction, the oligosaccharidic haptens are separated by gel-chromatography and the effluents are analyzed to determine the presence of methylpentoses, phosphorus and amino groups.

The oligosaccharidic haptens so obtained are subsequently transferred into dimethylsulphoxide and esterified in the presence of esters of organic acids, such as derivatives of adipic acid.

Preferably, the disuccinimidyl ester of the hydrazide of adipic acid is used, at a molar concentration in excess relatively to the amino groups introduced into the oligosaccharidic haptens, generally ranging from 2:1 to 10:1.

The oligosaccharidic haptens so activated are precipitated from the reaction mixture by the addition of 1,4-dioxane, using a 1,4-dioxane/dimethylsulphoxide ratio of 10:1 by volume.

The activated oligosaccharidic haptens are then centrifuged off from the reaction mixture, and analyzed to determine the disappearing of the amino groups and the conversion thereof into active esters.

The present invention relates moreover to a process for the preparation of glycoproteinic conjugates having trivalent immunogenic activity comprising the binding, contemporaneously or sequentially, by a covalent bond, to a protein selected among CRM 197, tetanus toxoid or pertussis toxin, at least one oligosaccharidic hapten derived from the capsular polysaccharide of a gram-positive bacterium, and at least one oligosaccharidic hapten derived from the capsular polysaccharide of a gram-negative bacterium, after the preliminary activation of the oligosaccharidic haptens by the introduction of terminal ester groups.

The reaction of conjugation between the protein and the oligosaccharidic haptens is carried out by adding to a protein, either contemporaneously or sequentially, the oligosaccharidic haptens, previously activated, operating with a protein/hapten molecular ratio of 1:10.

Typically, the conjugation reaction is carried out in the liquid phase, in the presence of an organic solvent, at a temperature comprised within the range of from 10° C. to 40° C., for a corresponding time period of from 2 to 24 hours. Preferably, the process is carried out at a temperature of 15° C. for a time of 15 hours, in the presence of dimethylsulphoxide.

At the end of the conjugation reaction, from the reaction mixture, the glycoproteinic conjugates are separated by gel-chromatography, the chromatographic effluents showing a chemical activity towards the protein and towards the bound oligosaccharidic haptens are combined. The effluents are sterilized by filtration, by using filter membranes of 0.22 μm.

The substitution degree in the proteinic molecule is verified for the polysaccharidic haptens by the chemical analysis of the glycoproteinic conjugate and subsequent conversion into mol of the percentages of the three components.

According to the present invention, the substitution degree of the glycoproteinic conjugate having trivalent immunogenic activity is of at least one oligosaccharidic hapten derived from the capsular polysaccharide of a gram-positive bacterium and of at least one oligosaccharidic hapten derived from the capsular polysaccharide of a gram-negative bacterium per each mol of protein. Generally, the number of oligosaccharidic haptens derived from the capsular polysaccharide of a gram-positive bacterium is comprised within the range of from 1 to 6, and that of the oligosaccharidic haptens derived from the capsular polysaccharide of a gram-negative bacterium of from 1 to 2 per each mol of protein.

The glycoproteinic conjugates of the present invention are useful as vaccines against epidemiologically meaningful capsulate gram-positive bacteria and capsulate gram-negative bacteria.

In particular, they can be used as vaccines to immunize the infantile population. Such molecules contain the oligosaccharidic haptens derived from capsular polysaccharides, the immune response of which is thymus-independent.

Said polysaccharides, by themselves poorly immunogenic in children, when are used for the preparation of the glycoproteinic conjugates of the present invention, yield on animal models a thymus-dependent immune response.

In particular, a test carried out by the ELISA method has demonstrated the production of antisera of antibodies specific to capsular polysaccharides, when the glycoproteinic conjugates of the present invention are used.

According to the present invention, vaccines are prepared by mixing a therapeutically effective amount of the glycoproteinic conjugate having trivalent immunogenic activity, with a liquid carrier selected among a physiologic solution, or other injectable liquid carriers.

To the said mixture, additives selected among those known from the present art for the preparation of vaccines can be added. Additives suitable to that purpose are such stabilizer compounds as lactose os sorbitol, and such adjuvants as aluminum hydroxide, phosphate, or an alginate.

Preferably, $AlPO_4$ is used.

The vaccines so obtained are administered by intramuscular or subcutaneous way.

The concentration of the glycoproteinic conjugates for the preparation of vaccines for children is comprised within the range of from 25 to 200 μg. Greater doses can be administered on the basis of the body weight.

The vaccine can be administered as one single dosis, or it can be divided into a plurality of doses.

To the purpose of illustrating the present invention, without however desiring limiting it, a glycoproteinic compound has been synthetized, wherein protein CRM 197 is bound by a covalent bond to at least one oligosaccharidic hapten derived from the capsular polysaccharide of the gram-positive bacterium *Streptococcus pneumoniae* Type 6A, and at least one oligosaccharidic hapten derived from the capsular polysaccharide of the gram-negative bacterium *Neisseria meningitidis* group C.

The immunogenic properties of said glycoproteinic conjugate have been tested on animals, evaluating the immune responses to protein CRM 197, as well as to the capsular polysaccharides of *S. pneumoniae* Type 6A, and of *N. meningitidis* group C.

The chemical hlycosilanizing appears distributed on both the A and B subunits forming the protein CRM 197.

The molecular weight of the glycoproteinic conjugate, computated on the basis of the molecular weights shown at line 1, is of about 78,000.

Figure 2:
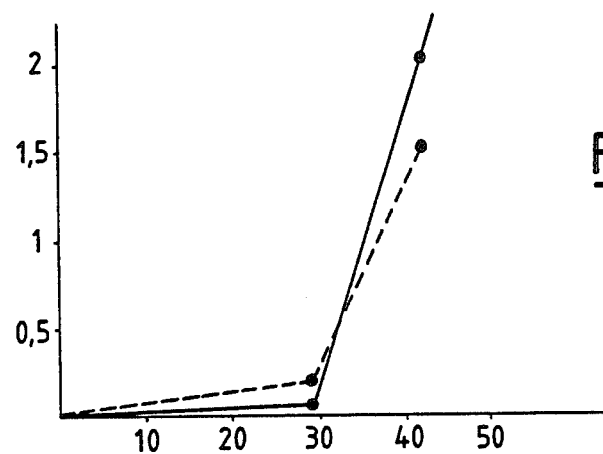

FIG. 2: The chart is shown which is obtained by reporting on the abscissae the time (days) and on the ordinates the concentrations of IgG immunoglobulins, expressed as ELISA units.

By ●———● the values are shown of anti-*S. pneumoniae* Type 6A IgG, and by ●-----● the values are shown of anti-*N. meningitidis* group C IgG.

Figure 3:
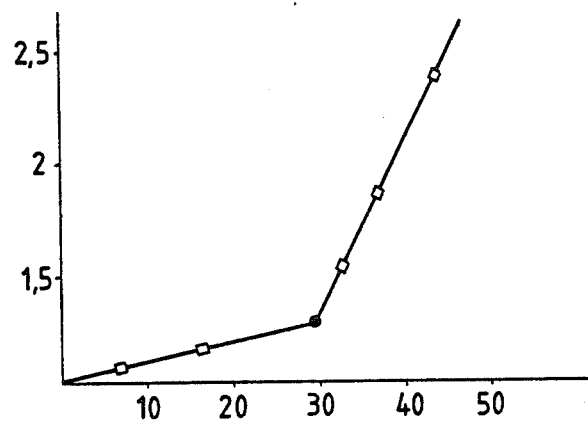

FIG. 3: In this figure, the chart is shown which is obtained for the determination of the bacteridical activity of the rabbit antisera on living strains of *N. meningitidis*.

On the abscissae the time (days) and on the ordinates the reciprocal of the logarithm of the dilution are reported, and by □------□ the anit-group C bactericidal activity is shown.

Figure 4:
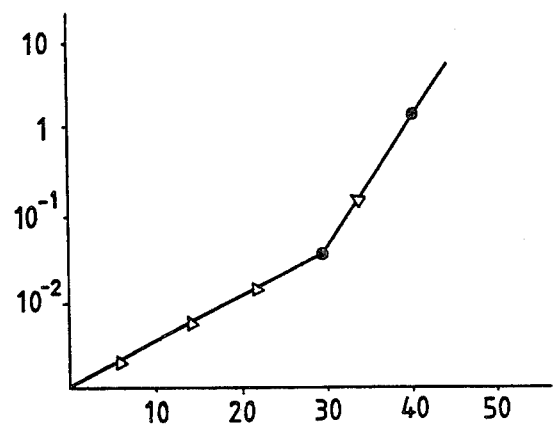

FIG. 4: the chart is shown which is obtained for the determination of the anti-diphtherin in antisera of Guinea-pigs immunized by the glycoproteinic conjugate having trivalent immunogenic activity.

On the abscissae the time (days) and on the ordinates the concentrations, expressed as S.I. units/ml are reported.

By △------△ the anit-diphtherin is indicated.

Each point represents the geometrical average of the titrations obtained for each group of 10 animals.

EXAMPLE 1

Preparation of the Oligosaccharidic Haptens Derived from the Capsular Polysaccharide of *Streptococcus pneumoniae* Type 6A Two mg of capsular polysaccharide of *S. pneumoniae* Type 6A is dissolved in 1 ml of aqueous solution containing 10 mM of acetic acid at pH 3.4.

The reaction of hydrolysis is carried out by maintaining the solution inside sealed ampuls dipped in oil bath, at a temperature of 100° C., for a time of 39 hours.

At the end of said time, the so-obtained oligosaccharides are separated from the reaction mixture, by chromatography over Sephadex G 15 (Pharmacia, Uppsala), conditioned with a 200 mM solution of NaCl at pH 7.0, by operating at 4° C.

The chromatographic effluents are then analyzed according to the procedures as reported by Kabat in Exp. Immunochemistry, Ed. E. A. Rabat & Mayer, pages 538–541, 1964), Chen et al. (Anal. Chem. 28, 1756–1758, 1956) and by Porro et al. (Anal. Biochem. 118, 301–306, 1981) to the purpose of verifying the presence of methyl-pentoses, phosphorus and reducing groups.

The results obtained show a phosphorus/rhamnose molecular ratio of 1 rhamnose/reducing groups of 3.

Upon analysis over Sephadex G-50, said oligosaccharides show a distribution constant (Kd) of 0.48, corresponding to a molecular weight (MW) of about 1500.

Upon N.M.R. analysis, the oligosaccharides result formed by about 8 monosaccharidic residues, among which the galactose residue, which is the immunodominant sugar, is found.

The N.M.R. analysis is typically carried out by dissolving 50 mg of the oligosaccharide in 1 ml of deuterium oxide ($D_2O$), using 5-mm probes at 35° C., a Varian Spectormeter model CFT 20, and operating at 20 Megahertz (MHz), using, as the inner standard, methanol, which has a $\delta = 39.5$ parts per million (ppm).

EXAMPLE 2

Preparation of the Oligosaccharidic Haptens Derived from the Capsular Polysaccharide of *Neisseria meningitidis* Group C The test is carried out as in preceding Example 1, but using, for the hydrolysis of the capsular polysaccharide of *N. meningitidis* group C, a 0.5 mM solution of acetic acid, at pH=5, for a time of 8 hours.

The oligosaccharidic haptens so obtained show, over Sephadex G-50, a Kd of 0.46, corresponding to a molecular weight of about 1500.

The chemincal analysis of the chromatographic effluents shows the presence of terminal reducing groups, and of a residue of N-acetyl-neuraminic acid, also known as sialic acid.

Upon N.M.R. analysis, said haptens result constituted by 10–12 monosaccharidic residues, among which the immunodominant residue N-acetyl-neuraminic acid.

EXAMPLE 3

Determination of the Immunochemical Properties of the Oligosaccharidic Haptens Derived from the Capsular Polysaccharides of *S. pneumoniae* 6A and *N. meningiditis* group C The test is carried out as described by Porro et al., in Molec. immunol., in press 1985.

Used are plastic plates for immunoelectrophoresis, subdivided into three compartments, A, B and C compartments, each containing 2 ml of 0.1% (w/v) agarose (Agarose M-LKB, Bromma).

Into compartment A, 0.05% (v/v) is introduced of rabbit antiserum, detector for the capsular polysaccharide of *S. pneumoniae* Type 6A, or for the capsular polysaccharide of *N. meningitidis* group C (Staten Seruminstitut, Copenhagen).

Into compartment B, 0.05% (v/v) is introduced of rabbit antiserum, detector for the capsular polysaccharidic antigen of *S. pneumoniae* Type 6A or of the capsular polysaccharidic antigen of *N. meningitidis* group C, previously incubated at 37° C. for 15 minutes, with respectively 5 nanograms of capsular polysaccharide of *S. pneumoniae* Type 6A and 5 nanograms of capsular polysaccharide N. meningitidis group C.

Into compartment C, 0.05% (v/v) is introduced of rabbit antiserum, detector for the capsular polysaccharide of *S. pneumoniae* Type 6A, or of rabbit anitserum, detector for the capsular polysaccharide *N. meningitidis* group C., previously incubated at 37° C. for 15 minutes with 5, 50, 500 and 5000 nanograms of the corresponding oligosaccharidic haptens.

The capsular polysaccharides Type 6A and group C used as reference are diluted four times, each time by a 1:2 ration (2, 4, 8, 16 total μg), and 10 μl of each dilution are introduced into each one of the 4 wells provided in agarose of Compartments B and C.

The plates so prepared are submitted to electrophoresis, operating at 70 V/cm, for a time period of from 1 to 2 hours. At the end, the plates are dried at 37° C., and the immunoprecipitated rockets are determined and quantified.

The sensitivity of this method is of about 20 ng/ml in the determination of this capsular polysaccharide of *S. pneumoniae* type 6A, and of about 50 ng/ml in the determination of polysaccharide of *N. meningitidis* group C.

The inhibition of the oligosaccharidic haptens was evidenced when the immunoprecipitated rockets were higher in agarose compartment C, which contains the reference antiserum preincubated with the oligosaccharidic haptens, than in compartment B, containing the reference antiserum preincubated with the polysaccharidic antigens.

The minimum inhibiting concentration of the oligosaccharidic haptens obtained as reported in Examples 1 and 2, and their immunochemical specificity, expressed as the amount by weight of the haptens, to the antigens recognized by the reference rabbit antibodies is then determined according to as described by Porro et al. in Molec. Immunol., in press, 1985.

In particular, it has been found that, for the oligosaccharidic haptens derived from the capsular polysaccharide of *S. pneumoniae* type 6A, the lower specificity value indicated the presence, in the structure, of the immunodominant sugar galactose, and for the oligosaccharidic haptens derived from the capsular polysaccaride *N. meningitidis*, the presence of the immunodominant acid: N-acetyl-neuraminic acid.

The specificity of the oligosaccharidic haptens, when compared to that of the respective polysaccharidic antigens was of respectively $1.08 \times 10^{-3}$ for the oligosaccharidic hapten derived from the capsular polysaccharide of *S. pneumoniae* Type 6A and $1.06 \times 10^{-3}$ for the oligosaccharidic hapten derived from the polysaccharide of *N. meningitidis* group C.

EXAMPLE 4

Preparation of Protein CRM 197

CRM 197, produced by the strain *Corynebacterium diphtheriae* C7 ($\beta^{tox-197}$), is separated from the culture medium by molecular filtration, by using a Millipore XM-50 (NMWL $5 \times 10^{-4}$) membrane.

The protein is then precipitated, by adding to the filtrate a solution of ammonium sulphate up to 65% of saturation.

The precipitated protein is then separated by centrifugation, and dissolved in 0.01 M phosphate buffer (pH 7.2).

Protein CRM 197 is subsequently purified by ion-exchange chromatography.

Used is a $2.5 \times 100$ DEAE Sepharose 6B/CL column (Pharmacia, Uppsala), conditioned in 0.01 M phosphate buffer at pH 7.2, and as the eluent a buffer solution with a 0.09 M concentration of NaCl.

80% of so-obtained CRM 197 is in its native molecular form, as determined by sodium dodecyl sulphate-electrophoresis over polyacrylamide gel (SDS - PAGE) under reducing conditions, according to as reported by Pappenheimer et al. (Immunochemistry 9, 891–906, 1972).

The purity of the protein is of about 400 flocculation limit (Lf)/mg.

EXAMPLE 5

Activation of the Oligosaccharidic Haptens Derived from the Capsular Polysaccharide of *S. Pneumoniae* Type 6A and from the Capsular Polysaccharide *N. meningitidis* group 6C and Their Conjugation with CRM 197

(a) Introduction of the primary amino groups into the terminal reducing groups of the oligosaccharidic haptens.

The oligosaccharidic haptens, obtained as reported in Examples 1 and 2, are separately dissolved in distilled water, to an end concentration of 10 mg/ml. To each solution, 50 mg/ml of ammonium chloride, and 20 mg/ml of $NaBH_3CN$ are then added.

The solution containing the oligosaccharidic haptens derived from capsular polysaccharide *S. pneumoniae* Type 6A is adjusted to pH 9 by 1 N NaOH and is kept, inside sealed ampuls, under mild stirring, at a temperature of 50° C. over two weeks. The solution containing the oligosaccharidic haptens derived from the capsular polysaccharide of *N. meningitidis* group C is adjusted to pH 8 andis kept, inside sealed ampuls, under mild stirring, at a temperature of 37° C. for one week.

At the end of the reaction, the oligosaccharidic haptens are purified by gel-chromatography, using a Sephadex G15 column conditioned in buffer solution with 10 mM NaCl at pH 7.0.

The chromatographic effluents having $Kd \leq 0.1$ and a chemical activity for respectively methyl pentose groups, phosphorus and amino groups, or N-acetyl-neuraminic acid and amino groups are collected and combined.

(b) Conversion of amino-group-hapten derivatives into the corresponding monofunctional esters.

The oligosaccharidic haptens into which the amino groups have been introduced are diluted to a concentration of 10 mg/ml in an aqueous solution of dimethyl-sulphoxide (at 80-95% v/v).

Said solutions are added dropwise, over a time ranging from 1 to 2 hours, to dimethylsulphoxide containing di-succinimidyl ester of adipic acid (DEA) in molar excess relatively to the amino groups introduced into the oligosaccharidic haptens (10:1).

The esterification reaction is carried out by keeping the solutions at 20°-25° C. for a time period of 4 hours. At the end of said time period, the esterified oligosaccharidic haptens are precipitated by the addition of 1,4-dioxane to an end concentration of 90% (v/v), and are subsequently separated from the reaction mixture by centrifugation.

The conversion of the amino groups into the corresponding active esters is then verified by the method as reported by Miron-wilchek (Anal. Biochem, 126, 433–435, 1982).

(c) Conjugation of the esterified oligosaccharidic haptens to CRM 197.

To an aqueous solution containing 2 mg/ml of CRM 197, a solution is added to dimethylsulphoxide containing the activated oligosaccharidic hapten derived from the capsular polysaccharide of *S. pneumoniae* Type 6A in 10:1 molar ratio to the protein, until an end concentration of dimethylsulphoxide in water of 20% (v/v) is obtained.

The mixture so obtained is kept, under mild stirring, at room temperature (20°–25° C.) for 15 hours. At the end of said time period, the organic solution containing the activated oligosaccharidic hapten derived from the capsular polysaccharide of *N. meningitidis* group C is added in a 10:1 molar ratio to the protein, and the resulting mixture is kept 15 hours at room temperature.

According to an alternative route, the conjugation reaction can be carried out by adding, at the same time, to the CRM-197-containing solution, the two activated oligosaccharidic haptens respectively derived from the capsular polysaccharide of *S. pneumoniae* Type 6A and from the capsular polysaccharide of *N. meningitidis* group C.

The glycoproteinic conjugates so obtained are separated by gel-chromatography, using a Sephadex G-100 column (Pharmacia, Uppsala), conditioned in 0.01 M phosphate buffer containing 0.2 M NaCl (pH=7.0). The eluted fractions showing a chemical activity for the proteins, phosphorus and sialic acid are combined and filtered through a millipore membrane having a porosity of 0.22 µm.

The chemical analysis of the glycoproteinic conjugate so obtrained shows a content of protein of 87% (w/w), of Type-6A oligosaccharidic hapten of 8% (w/w), and of group-C oligosaccharidic hapten of 5% (w/w).

These values, converted into mol, show a degree of substitution, per each mol of protein CRM 197, of 4 mol of oligosaccharidic haptens of Type 6A, and of 2 mol of oligosaccharidic haptens of group C.

Figure 1:
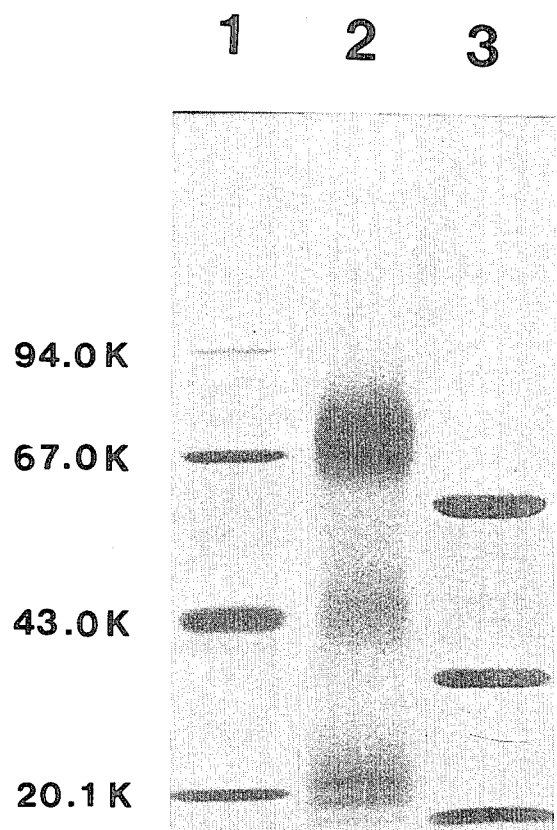
FIG. 1: the electrophoretic behaviour is shown of the glycoproteinic conjugate (5 μg, line 2) and of the native protein CRM 197 (5 μg, line 3).

The physical-chemical characterization of the glycoproteinic conjugate has been determined by SDS-PAGE and a gradient of acrylamide of 3–9%, according to Laemuli's procedure (Nature 227, 680-685, 1970) (FIG. 1).

The immunochemical specificity of monoclonal anitbodies for different epitopes of protein CRM 197, as compared to that observed for the glycoproteininc conjugate wherein the protein is CRM 197, is reported in Table 1.

The values, obtained from three experimental tests, are determined by using the ELISA methodology.

The specificity percentage of the monoclonal antibodies for the proteinic conjugate was computed assuming a value of 100 for the specificity observed by measuring the absorbance values, in the ELISA procedure, for CRM 197.

TABLE 1

| Monoclonal Antibodies | Recognized Epitopes in CRM 197 | Number of Residual Aminoacids in the Epitopes | | % Specificity for | |
|---|---|---|---|---|---|
| | | Lys | Arg | CRM 197 | Glycoproteinic Conjugate |
| Group I (Clone 6 B 12) | 1–156 | 14 | 2 | 100 | 31 |
| Group II b (Clone 2 A 5) | 157–193 | 2 | 5 | 100 | <10 |
| Group III a (Clone 2 A 7) | 293–345 | 1 | — | 100 | 21 |
| Group IV C I) (Clone 2 E 10) | 465–535 | 6 | 2 | 100 | 95 |

As it can be seen from the preceding Table, the most important epitope of CRM 197, localized in the 465–535 sequence of the protein, is present in the protein CRM 197 of the glycoproteinic conjugate.

This epitope is the most important immunodeterminant of the diphtherin, it being able to induce neutralizing antibodies by the inhibition of the cellular bond of the same toxin on sensibe cells.

EXAMPLE 5

Immunological Characteristics of Animal Sera Obtained After Immunization by the glycoproteininc Conjugate Having Trivalent Immunogenic Activity Obtained in Example 5

Two groups of 10 rabbits of weight of about 2 kg, and one groups of 10 Guinea-pigs, of weight of 350g, are inoculated by subcutaneous way with two doses of the glycoproteinic conjugate absorbed on a support of AlPO$_4$ (37.5 mg of glycoproteinic conjugate/1.5 mg of AlPO$_4$).

Each dosis contains 12.5 Lf of CRM 197, 4.8 ng of oligosaccharidic hapten derived from the capsular polysaccharide of *S. pneumoniae* Type 6a, and 3 ng of oligosaccharidic hapten derived from the capsular polysaccharide of *N. meningitidis* group C.

The second dosis is inoculated 28 days after the 1st dosis. Serum collections are carried out on the rabbits soon after the administration of the two doses, and 11 days after the administration of the second dosis.

Rabbit antisera are analyzed by an immunoenzymatic method (ELIAS) according to A. Voller et al., "Microplate Enzyme-Linked Immunosorbent Essay for Chagas Disease", Lancet 1, 426 (1975), to the purpose of determining the presence of IgG immunoglobulins specific to the oligosaccharidic hapten derived from the capsular polysaccharide of *S. pneumoniae* Type 6A and to the oligosaccharidic hapten derived from the capsular polysaccharide of *N. meningitidis* group C (FIG. 2).

The bactericidal activity of rabbits antisera has been verified on living strains of *N. meningitidis* according to the method as described by Wong et al. (J. Biol. Stand. 5, 197–215, 1977) and the results have confirmed the development of a meaningful bactericidal activity soon after the administration of each of the doses of glycoproteinic conjugate (FIG. 3).

The antisera from Guinea-pigs are analyzed for determining the content of anti-diphtherin, according to the U.S. Pharmacopoeia method.

A horse antiserum for diphtherin is used as the standard in the titration of the diphtherin used in the biological analysis, and in FIG. 4, the chart obtained is illustrated.

In all the animals, before the immunization, the absence of specific antibodies has been determined.

The immunization of control animals with only oligosaccharidic haptens or capsular polysaccharides had shown the absence of immunogenicity of said purified compounds.

We claim:

1. Glycoproteinic conjugates having trivalent immunogenic activity, obtained by covalently binding a proteinic antigen selected among CRM 197, tetanus toxoid, and pertussis toxin, with at least one first oligosaccharidic hapten obtained from the capsular polysaccharide of a gram-positive bacterium, and with at least one second oligosaccharidic hapten obtained from the capsular polysaccharide of a gram-negative bacterium, said first and second oligosaccharidic haptens having been preliminarily activated by the introdution of terminal ester groups.

2. The glycoproteinic conjugates of claim 1, wherein the first oligosaccharidic hapten is obtained from bacteria selected from Streptococcus pneumoniae and Streptococcus β-emoliticus and the second oligosaccharidic hapten is obtained from bacteria selected from Nesisseria meningitidis, Haemophilus influenzae, Pseudomonas aeruginosa and Escherichia coli.

3. The glycoproteinic conjugates of claim 2, wherein the proteinic antigen is CRM 197, the first oligosaccharidic hapten is obtained from Streptococcus pneumoniae and the second oligosaccharidic hapten is obtained from Neisseria meningitidis, said proteinic antigen, said first oligosaccharidic hapten and said second oligosaccharidic hapten having a molecular ratio of 1:1–6:1–2.

4. The glycoproteinic conjugates of claim 1, 2, or 3 wherein said first and second activated oligosaccharidic haptens each have a molecular weight of about 1000 to 2000.

5. A process for the preparation of glycoproteinic conjugates having trivalent immunogenic activity comprising:

(a) activating at least one first oligosaccharidic hapten obtained from the capsular polysaccharide of a gram-positive bacterium and at least one second oligosaccharidic hapten obtained from the capsular polysaccharide of a gram-negative bacterium by the introduction of terminal ester groups; and (b) covalently binding said at least one first oligosaccharidic hapten and said at least one second oligosaccharidic hapten to a proteinic antigen selected from CRM197, tetanus toxoid and pertussis toxin.

6. The process of claim 5 wherein the first and second oligosaccharidic haptens are covalently bound to the proteinic antigen sequentially or concurrently.

7. The process of claim 5, wherein the first oligosaccharidic hapten is obtained from bacteria selected from Streptococcus pneumoniae and Streptococcus β-emoliticus and the second oligosaccharidic hapten is obtained from bacteria selected from Neisseria meningitidis, Haemophilus influenzae, Pseudomonas aeruginosa and Escherichia coli.

8. The process of claim 7, wherein the proteinic antigen is CRM 197, the first oligosaccharidic hapten is obtained from Streptococcus pneumoniae, and the second oligosaccharidic hapten is obtained from Neisseria meningitidis.

9. The process of claim 5, 6, 7, or 8 comprising covalently binding the first and second oligosaccharides to the proteinic antigen in a liquid medium in the presence of dimethylsulfoxide, at a temperature of from 20° C. to 25° C. for 4 to 24 hours.

10. A vaccine against capsulate gram-negative and gram-positive bacteria comprising a therapeutically effective amount of the glycoproteinic conjugate of claim 1, 2, or 3 and a pharmacologically acceptable carrier.

11. A vaccine against capsulate gram-negative and gram-positive bacteria comprising a therapeutically effective amount of the glycoproteinic conjugate of claim 4 and a pharmacologically acceptable carrier.

12. A method of inducing active immunization against infection caused by capsulate gram-positive and gram-negative bacteria in mammals comprising administering to said mammals the vaccine of claim 10.

* * * * *